(12) United States Patent
Guthlein

(10) Patent No.: US 9,579,133 B2
(45) Date of Patent: Feb. 28, 2017

(54) INTERNAL FIXATION DEVICE

(71) Applicant: James Guthlein, Wayne, PA (US)

(72) Inventor: James Guthlein, Wayne, PA (US)

( * ) Notice: Subject to any disclaimer, the term of this patent is extended or adjusted under 35 U.S.C. 154(b) by 22 days.

(21) Appl. No.: 13/756,600

(22) Filed: Feb. 1, 2013

(65) Prior Publication Data
US 2014/0221919 A1 Aug. 7, 2014

(51) Int. Cl.
*A61B 17/80* (2006.01)
*A61B 17/00* (2006.01)

(52) U.S. Cl.
CPC .......... *A61B 17/80* (2013.01); *A61B 17/8057* (2013.01); *A61B 2017/00004* (2013.01)

(58) Field of Classification Search
CPC ................................. A61B 17/8028
USPC ...................................... 606/70, 71
See application file for complete search history.

(56) References Cited

U.S. PATENT DOCUMENTS

| | | | |
|---|---|---|---|
| 4,297,993 A * | 11/1981 | Harle | A61B 17/80 606/70 |
| 4,403,606 A | 9/1983 | Woo et al. | |
| 4,403,607 A | 9/1983 | Woo et al. | |
| 4,662,887 A | 5/1987 | Turner et al. | |
| 4,678,660 A | 7/1987 | McGary et al. | |
| 4,957,496 A * | 9/1990 | Schmidt | 606/70 |
| 5,013,313 A | 5/1991 | Surer | |
| 5,139,497 A | 8/1992 | Tilghman et al. | |
| 5,290,281 A * | 3/1994 | Tschakaloff | 606/28 |
| 5,346,492 A | 9/1994 | Morgan | |
| 5,976,141 A | 11/1999 | Haag et al. | |
| 6,153,664 A | 11/2000 | Wise et al. | |
| 6,440,135 B2 | 8/2002 | Orbay et al. | |
| 6,719,759 B2 | 4/2004 | Wagner et al. | |
| 6,953,784 B2 | 10/2005 | Thompson et al. | |
| 6,991,681 B2 | 1/2006 | Yoe | |
| 7,067,169 B2 | 6/2006 | Liu et al. | |
| 7,837,717 B2 | 11/2010 | Deffenbaugh et al. | |
| 8,182,517 B2 | 5/2012 | Sixto, Jr. et al. | |
| 8,192,472 B2 | 6/2012 | Sixto, Jr. et al. | |
| 8,197,480 B2 | 6/2012 | Roller et al. | |
| 8,197,521 B2 | 6/2012 | Sixto, Jr. et al. | |

(Continued)

FOREIGN PATENT DOCUMENTS

| | | |
|---|---|---|
| EP | 1488753 | 12/2004 |
| WO | WO01/39680 | 6/2001 |

(Continued)

OTHER PUBLICATIONS

International Search Report and Written Opinion for PCT/US2014/012179, mailed Apr. 16, 2014.

(Continued)

*Primary Examiner* — David Bates
*Assistant Examiner* — Olivia C Chang
(74) *Attorney, Agent, or Firm* — Joseph E. Maenner; Maenner & Associates, LLC

(57) ABSTRACT

A medical implant according to the present invention includes a substrate having a first plurality of openings and a second plurality of openings formed therein. An outer covering substantially encompasses the substrate. The outer covering has an absence of sharp edges and extends into the first plurality of openings and around the second plurality of openings. A kit including the implant and at least one fastener is also disclosed.

9 Claims, 6 Drawing Sheets

(56) References Cited

U.S. PATENT DOCUMENTS

| | | |
|---|---|---|
| 8,221,782 B2 | 7/2012 | Kerr et al. |
| 2004/0073318 A1 | 4/2004 | Reinmuller |
| 2005/0065522 A1 | 3/2005 | Orbay |
| 2007/0265629 A1 | 11/2007 | Martin et al. |
| 2008/0215093 A1 | 9/2008 | Lin et al. |
| 2008/0234753 A1* | 9/2008 | Trieu ............... 606/297 |
| 2008/0262630 A1* | 10/2008 | Fulmer et al. ........... 623/23.52 |
| 2009/0299369 A1* | 12/2009 | Orbay et al. ............ 606/70 |
| 2010/0114316 A1 | 5/2010 | Swords |
| 2010/0266657 A1 | 10/2010 | Xia et al. |
| 2012/0016365 A1 | 1/2012 | Fried et al. |
| 2012/0083847 A1 | 4/2012 | Huebner et al. |
| 2012/0101361 A1 | 4/2012 | Rains et al. |
| 2012/0184960 A1* | 7/2012 | Dosta ............ A61B 17/8028 606/71 |
| 2012/0209396 A1 | 8/2012 | Myung et al. |
| 2012/0279881 A1* | 11/2012 | Janko et al. ............ 206/232 |

FOREIGN PATENT DOCUMENTS

| | | |
|---|---|---|
| WO | WO2007141317 | 12/2007 |
| WO | WO2009149296 | 12/2009 |
| WO | WO2011056995 | 5/2011 |
| WO | WO2011/154891 | 12/2011 |

OTHER PUBLICATIONS

International Preliminary Report on Patentability for PCT/US2014/012179, mailed Aug. 4, 2015. 7 pages.

\* cited by examiner

INTERNAL FIXATION DEVICE

FIELD OF THE INVENTION

The present invention relates to a device to be used in the field of surgical implantation for use in long bones, craniomaxiofacial, and spinal areas of the human body where internal fixation is needed. The invention is applicable to a wide range of surgical approaches not limited to reconstruction, trauma, deformity correction, and cosmetic surgeries.

BACKGROUND OF THE INVENTION

Internal fixation devices have been in existence from the earlier part of the 20th century, gaining further credibility in the medical community in the later half of the century. Internal fixation relies on four principles: preservation of the blood supply; anatomic reduction; stable fixation; and early and functional movement of the operative area. Devices used in this practice predominantly consist of metallic implants made from implant grade stainless steel, commercially pure grades of titanium and titanium alloys. In the practice of internal fixation there are three main branches, namely trauma, craniomaxiofacial, and spine. In Trauma, internal fixators fall into two categories of use, intermedulary nails, which are rods inserted into long bones thus securing the bone internally within itself; and secondly with what are known as plates and screws. Plates and screws can be found in all three branches of internal fixation. Plates in most cases must be used with screws, however screws do not have to be used with plates.

While these advancements in plate and screw technology, along with a deeper understanding of less invasive surgical techniques, have provided surgeons to deliver improved patient outcomes, there still exists a need to improve these internal fixation devices.

BRIEF SUMMARY OF THE INVENTION

Briefly, the present invention discloses a medical implant that includes a substrate having a first plurality of openings and a second plurality of openings formed therein. An outer covering substantially encompasses the substrate. The outer covering has an absence of sharp edges and extends into the first plurality of openings and around the second plurality of openings.

Further, the present invention discloses a kit having the implant described above and at least one fastener that is used to secure the implant to a bone.

Additionally, the present invention provides a medical implant comprising a substrate having a plurality of openings extending therethrough and an outer covering substantially encompassing the substrate. The outer covering has an absence of sharp exterior edges and extends around the plurality of openings such that a portion of the substrate surrounding each of the second plurality of openings is not encompassed by the outer covering.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
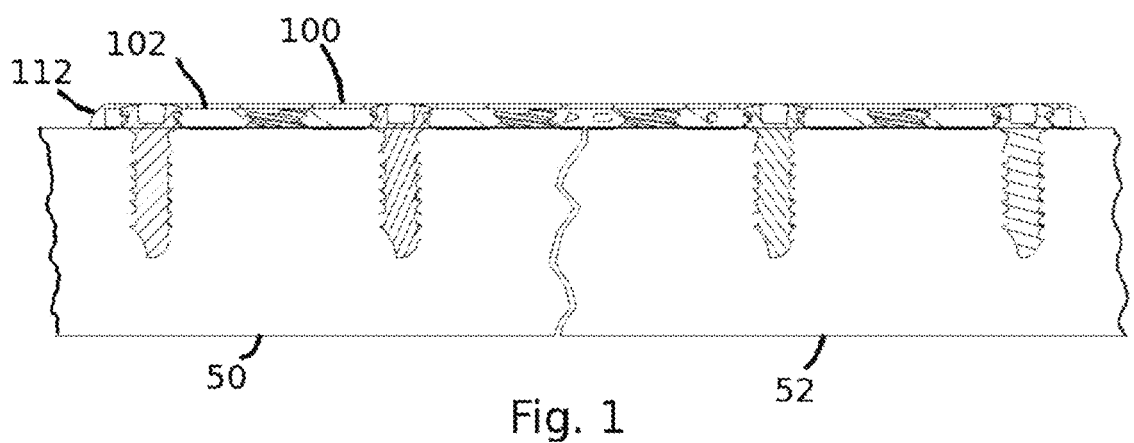
FIG. 1 is a side elevational view of an internal fixation implant according to a first exemplary embodiment of the present invention, coupling to pieces of broken bone together.

In the drawings, like numerals indicate like elements throughout. Certain terminology is used herein for convenience only and is not to be taken as a limitation on the present invention. The terms "proximal" and "distal" refer, respectively, to directions toward and away from a body. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments.

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Referring now to FIG. 1, a medical implant 100 according to a first exemplary embodiment of the present invention is used to internally fixate broken pieces 50, 52 of bone after pieces 50, 52 are set. Implant 100 is envisioned to be a temporary internal fixation device and may be removed after pieces 50, 52 fuse together, although those skilled in the art will recognize that implant 100 may permanently remain after pieces 50, 52 fuse together.

Figure 2:
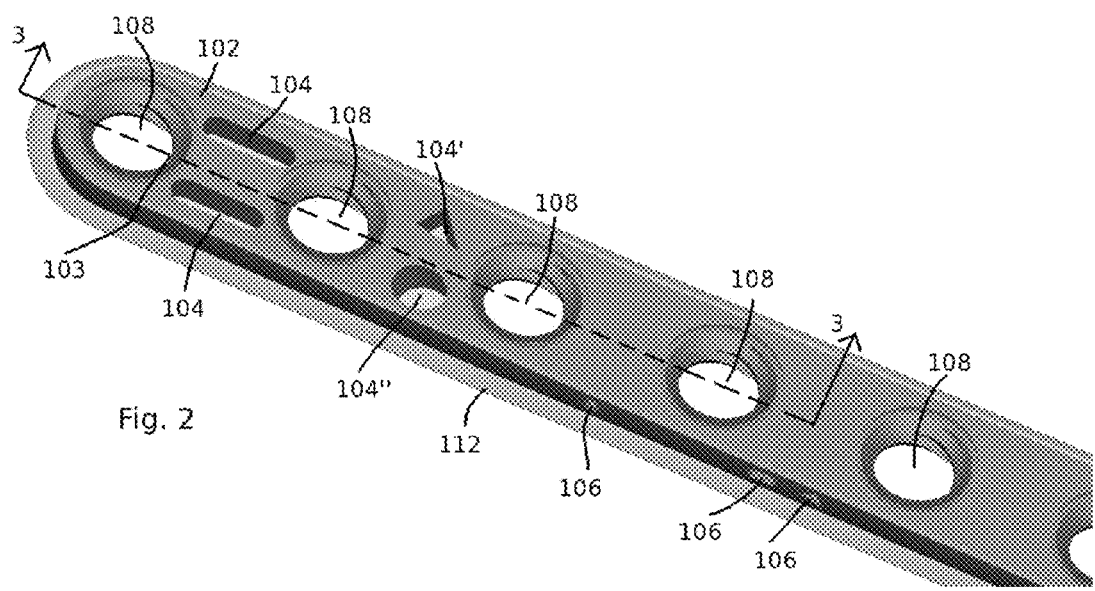
FIG. 2 is a perspective view of the internal fixation implant shown in FIG. 1.
Figure 3:
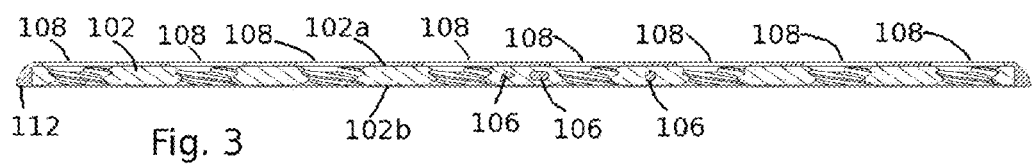
FIG. 3 is a sectional view of the internal fixation implant shown in FIG. 2, taken along lines 3-3.

Referring to FIGS. 2 and 3, medical implant 100 includes a substrate 102 and an outer covering 112 substantially encompassing substrate 102. Substrate 102 has a longitudinal axis 103 that extends therethrough. Substrate 102 includes an upper surface 102a and a lower surface 102b. Substrate 102 further includes a first plurality of openings 104, 106 and a second plurality of openings 108 formed therein. All of openings 104, 106, 108 may be chamfered at each of upper surface 102a and lower surface 102b (as shown in FIG. 5A) or, alternatively, only at an upper surface 102a (as shown in FIG. 6).

Substrate 102 may be constructed from a rigid material. While an exemplary rigid material may be one selected from the group consisting of a metal, a ceramic, and a composite material, those skilled in the art will recognize that other rigid, biocompatible and/or combinations of materials may be used.

Figure 4:
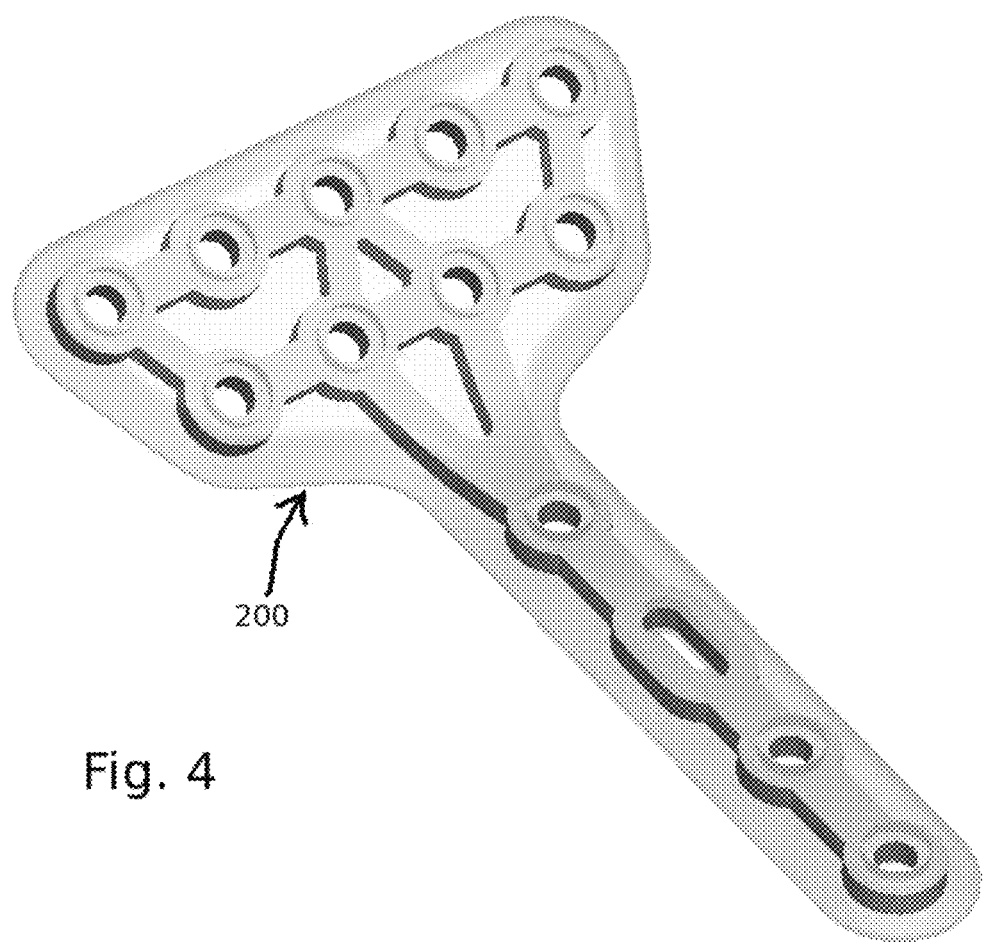
FIG. 4 is a perspective view of an internal fixation implant according to a second exemplary embodiment of the present invention.

Further, while implant 100 shown in FIGS. 2 and 3 is an elongated rod or bar and may be used to secure two elongated bone pieces 50, 52 (as shown in FIG. 1), such as a proximal end and a distal end of a tibia bone together, other implant shapes, such as implant 200, shown in FIG. 4, which is a generally "T-shaped" implant used for a distal radius (wrist) are also within the scope and intent of the present invention. Further, while substrate 102 is shown as a bar with a uniform cross-section, those skilled in the art will recognize that substrate 102 may have a non-uniform cross-section (shown in FIG. 5) as well.

Some of the first plurality of openings 104 extend through substrate 102 and allow outer covering 112 to extend therethrough to securely bind outer covering 112 to substrate 102. While openings 104 extend generally orthogonally to longitudinal axis 103, openings 104' and 104" may be formed at compound angles that extend obliquely relative to longitudinal axis 103. Others 106 of the first plurality of openings 104 may extend partially or entirely through substrate 102. Outer covering 112 extends into this plurality of openings 106 to further secure outer covering 112 to substrate 102. Similar to openings 104' and 104", at least some of openings 106 may be formed at compound angles that extend obliquely relative to longitudinal axis 103.

Second plurality of openings 108 extends through substrate 102 and is used to allow a fastener 120 (shown FIG. 6) to extend therethrough to secure substrate 102 to either piece 50, 52 of bone. In the event that fastener 120 is a screw, some of second plurality of openings 108 may include threads 109 (shown FIG. 6) into which fastener 120 is screwed.

Figure 5:
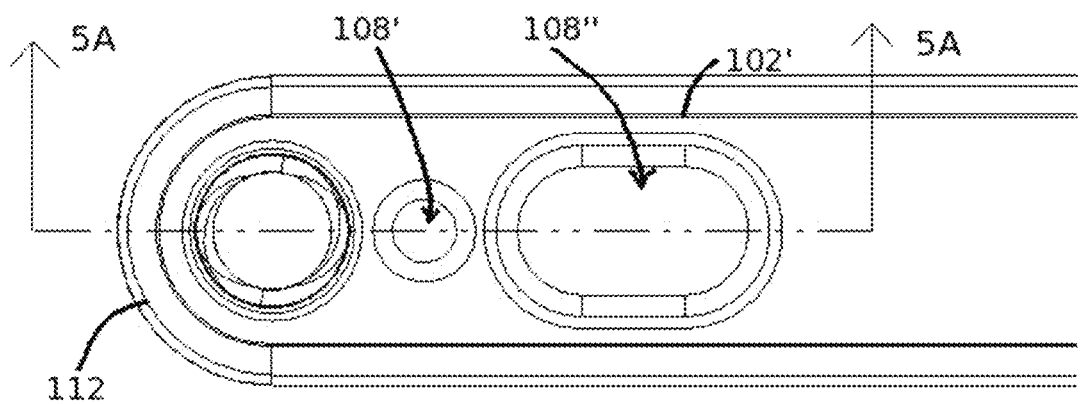
FIG. 5 is a top plan view of an alternative embodiment of an internal fixation implant according to the present invention.
Figure 5A:
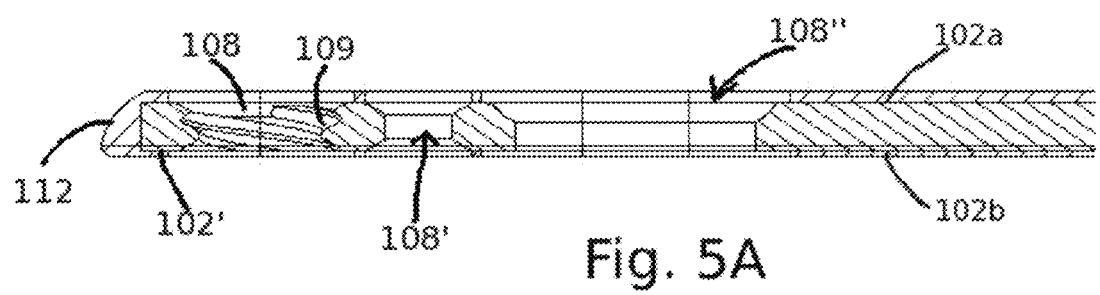
FIG. 5A is a sectional view of the internal fixation implant shown in FIG. 5, taken along lines 5A-5A of FIG. 5.
Figure 6:
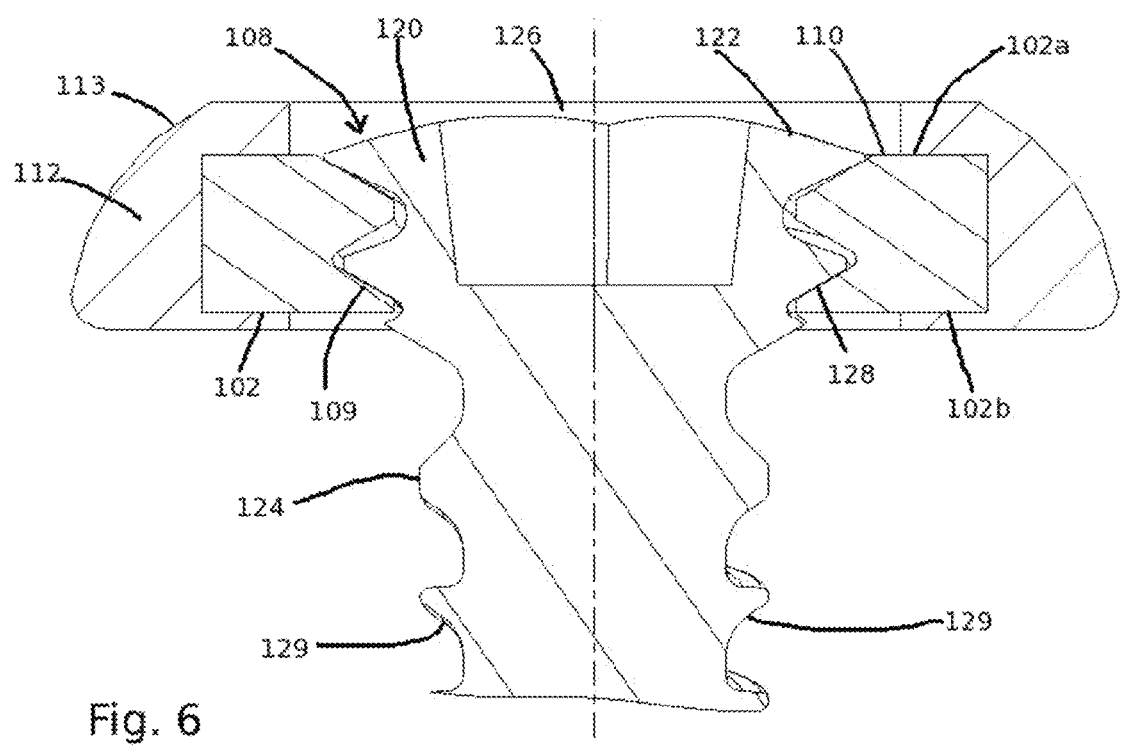
FIG. 6 is a side view, in section, of a fastener extending through internal fixation implant FIG. 1.

Alternatively, as shown in FIGS. 5 and 5A, with a substrate 102', others of second plurality of openings 108' may be unthreaded and are used to accept K-wires or other provisional fixation devices (not shown). Second plurality of openings 108, 108' may be generally circular. Alternatively, others of second plurality of openings 108" may be elongated slots that allow fastener 122 be inserted thereinto to allow adjustment of implant 100 along the length of pieces 50, 52 of bone.

Referring now to FIG. 6, fastener 120 may be a screw or other suitable fastening device. Additionally, fastener 120 may be constructed from stainless steel, titanium or other suitable, biocompatible material.

Fastener 120 includes a screw head 122 and an elongated screw shaft 124. Screw head 122 may include an opening 126 that is sized and shaped to receive a torquing device, such as, for example a screwdriver (not shown) or other type of driver. Screw head 122 may be tapered or chamfered, such that a portion of screw head 122 proximate to opening 126 is higher than the outer edge of head 122. Screw head 122 may also include threads 128 that are sized to engage mating threads 109 in opening 108.

Screw shaft 124 has an outer diameter that is smaller than the diameter of opening 108 so that screw shaft 124 can be inserted through opening 108. Additionally, screw shaft 124 may also be threaded with threads 129 that are used to grip a safe bone (not shown) so that fastener 120 secures implant 100 to the bone.

Outer covering 112 substantially encompasses substrate 102 and has an absence of sharp exterior edges. As shown FIG. 6, exterior edge 113 of outer covering 112 is generally chamfered and curved to eliminate any sharp edges.

As described above, outer covering 112 extends into first plurality of openings 104, 106, but not into second plurality of openings 108. Outer covering 112 extends around second plurality of openings 108 such that a portion of substrate 102 surrounding each of second plurality of openings 108 is not encompassed by outer covering 112. As shown FIG. 6, an uncovered portion 110 of substrate 102 around second opening 108 allows the head 122 of fastener 120 to directly engage substrate 102.

Outer covering 112 may be sufficiently thick over the top surface of substrate 102 such that, when fastener 120 is inserted through substrate 102, outer covering extends above screw head 122 such the screw head 122 extends between substrate 102 and the exterior surface of outer covering 112. Those skilled in the art, however, will recognize that screw head 122 may extend above the exterior surface of outer covering 112.

As shown FIG. 6, where outer covering 112 does not extend over substrate 102, outer covering 112 extends generally orthogonally to upper surface 102a and lower surface 102b. Those skilled in the art, however, will recognize that outer covering 112 can taper toward upper surface 102a and lower surface 102b to provide a smooth transition between outer covering 112 and substrate 102.

In an exemplary embodiment, outer covering 112 is constructed from an elastomer, such as, for example a silicone elastomer, a thermoset elastomer, a thermoplastic elastomer, or other biocompatible material.

Implant 100 can be manufactured, in the case of an elastomer, by taking substrate 102, masking the plurality of holes 104, 106, and inserting substrate 102 into a compression mold cavity in a compression machine (not shown) in conjunction with a slug of the elastomeric material. The compression mold cavity is in the final shape of outer covering 112. Once the compression machine is activated, applying compression to elastomeric slug, compressive forces will cause the elastomer to cover substrate 102, forming outer covering 112, wherefrom the masking can be removed from the plurality of openings in substrate 102.

Figure 7:
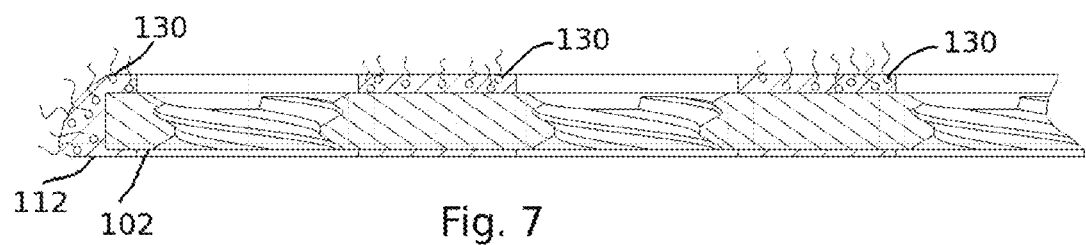
FIG. 7 is a side view, in section, of an alternative embodiment of the present invention.

In an exemplary embodiment, as shown FIG. 7, outer covering 112 is infused with a medicament 130. Medicament 130 may be an antimicrobial medicament to reduce the likelihood of infection. After implant 100 is inserted into the patient, medicament 130 exudes from outer covering 112 and is absorbed by the patient.

Figure 8:
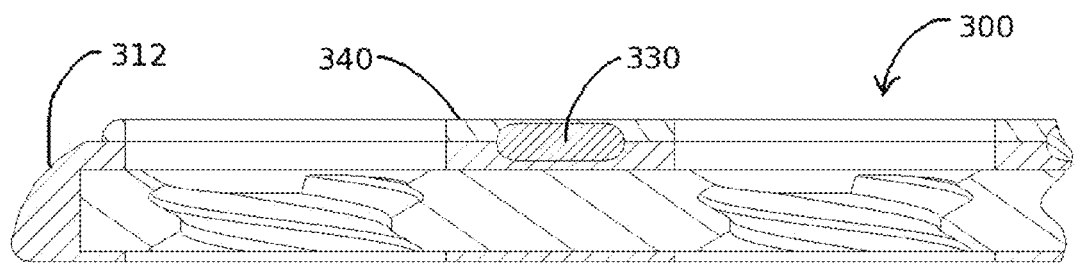
FIG. 8 is a side view, in section, of another alternative embodiment of the present invention.

In an alternative embodiment, shown FIG. 8, a medical implant 300, similar to medical implant 100 described above, includes a coating 340 disposed over outer covering 312. A medicament 330 is disposed between coating 340 and outer covering 312. Coating 340 may be constructed from hydroxyapatite, poly (L-lactides) or other suitable biodegradable material. Coating 340 is biodegradable such that coating 340 dissolves after implant 300 is inserted into the patient. Medicament 330 is then released from implant 300 and is absorbed by the patient. In order to prevent implant 300 from listening with respect to bone pieces 50, 52 (not shown FIG. 8) as coating 340 dissolves, coating 340 is not applied to the bottom portion of implant 300 where implant 300 engages bone pieces 50, 52.

Further, the present invention includes a kit that includes implant 100, 200, or 300 as well as at least one, and preferably a plurality of, fasteners 120. Fasteners 120 are used to secure implant to both broken bone pieces 50, 52. The kit can also include temporary fixation devices, such as, for example K-wires (not shown), torquing devices (not shown), and/or other materials necessary for the proper insertion of implant 100, 200, 300 into a patient.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A medical implant comprising:
a substrate having a first surface, an opposing second surface, and a first plurality of openings, wherein each opening in a first subset of the first plurality of openings extends fully therethrough between the first surface and the second surface and a second plurality of openings extending through the substrate between the first surface and the second surface; and
an outer covering molded over at least a portion of the substrate, the outer covering having a first portion substantially encompassing and fixedly connected to the first surface of the substrate, a second portion substantially encompassing the second surface of the substrate, and a connecting portion connecting the first portion and the second portion, the outer covering molded into the first plurality of openings and extending contiguously around each of the second plurality of openings such that the substrate surrounding each of the plurality of second openings is uncovered by the outer covering.

2. The medical implant according to claim 1, wherein the substrate is constructed from a material selected from the group consisting of a metal, a ceramic, and a composite material.

3. The medical implant according to claim 1, wherein the outer covering is constructed from an elastomer.

4. The medical implant according to claim 1, wherein a third plurality of openings extend only partially through the substrate.

5. The medical implant according to claim 1, wherein the substrate includes a longitudinal axis and wherein at least one of the first plurality of openings extends obliquely to the longitudinal axis.

6. The medical implant according to claim 1, wherein the substrate includes a longitudinal axis, and wherein at least one of the first plurality of openings extends orthogonally to the longitudinal axis and to the second plurality of openings.

7. The medical implant according claim 1, wherein the outer covering is infused with a medicament.

8. A medical implant comprising:
a substrate having a first surface and a second surface opposite the first surface, and having a first plurality of openings and a second plurality of openings formed therein; and
an outer covering molded over and substantially encompassing the first and second surfaces of the substrate, wherein the outer covering has an absence of sharp exterior edges, the outer covering molded into the first plurality of openings and extending around the second plurality of openings such that the outer covering is contiguous around each of the second plurality of openings;
a coating disposed over at least a portion of the outer covering, the coating being biodegradable and being selected from the group consisting of hydroxyapatite and poly (L-lactides); and
a medicament disposed between the coating and the outer covering such that, upon the biodegradation of the coating, the medicament is released from the implant.

9. The medical implant according to claim 8, wherein at least some of the first plurality of openings extend only partially through the substrate and wherein the outer covering extends into the some of the first plurality of openings.

* * * * *